United States Patent [19]

Watjen

[11] Patent Number: 4,675,605
[45] Date of Patent: Jun. 23, 1987

[54] EDDY CURRENT PROBE AND METHOD FOR FLAW DETECTION IN METALS

[75] Inventor: John P. Watjen, Sunnyvale, Calif.
[73] Assignee: SRI International, Menlo Park, Calif.
[21] Appl. No.: 698,369
[22] Filed: Feb. 5, 1985
[51] Int. Cl.$^4$ ........................................... G01N 27/82
[52] U.S. Cl. ................................................... 324/240
[58] Field of Search ............... 324/235, 236, 237, 238, 324/239, 240, 241, 242, 243, 228, 232, 234

[56] References Cited

U.S. PATENT DOCUMENTS 3,617,874 11/1971 Forster ................................ 324/241
4,286,216 8/1981 Auld et al. .......................... 324/237

FOREIGN PATENT DOCUMENTS 1272409 4/1972 United Kingdom .

OTHER PUBLICATIONS

Watjen et al, "Evaluation of a Novel Eddy Current Probe for Detecting Cracks Inside and at the Edges of Holes", *Review of Progress in Quantitative Nondestructive Evaluation*, (vol. 2B), 1983, pp. 1187–1202.
Watjen et al, "Evaluation of an Eddy-Current Tape--Head Probe", *Review of Progress in Quantitative Nondestructive Evaluation*, (vol. 3A), 1984, pp. 663–674.

Primary Examiner—Reinhard J. Eisenzopf
Assistant Examiner—Robert W. Mueller
Attorney, Agent, or Firm—Victor R. Beckman

[57] ABSTRACT

A flaw detecting system is shown which includes a probe having a pair of ferrite cores with in-line gaps in close proximity to each other. An insulating, non-magnetic, non-conducting holder fills the gaps and supports the ferrite cores in a manner such that the cores form a generally V-shape. Each core is provided with an excitation winding and a detection winding. The excitation windings are connected in series or parallel with an rf port for connection thereof to a radio frequency source. The detection windings, which are differentially wound, are connected in series circuit to a detector port for connection to a voltage measuring instrument. The ferrite cores at the in-line gaps directly engage the metal surface of a test piece, and the probe is scanned along the test piece. In the presence of a flaw in the metal surface the detection winding voltages are unbalanced, and the unbalance is detected by the voltage measuring instrument. The insulating holder is provided with a profile which conforms to that of a prominent feature of the test piece to facilitate movement of the probe along the feature, typically an edge or a corner.

4 Claims, 9 Drawing Figures

EDDY CURRENT PROBE AND METHOD FOR FLAW DETECTION IN METALS

ORIGIN OF THE INVENTION

This invention was made with Government Support under Subcontract SC-81-008 under Prime contract No. W-7405-ENG-82, awarded by the Department of Energy. The Government has certain rights in this invention.

TECHNICAL FIELD

This invention relates to an eddy current probe and method for detection of near-surface flaws in metals.

BACKGROUND OF THE INVENTION

Eddy current probes for flaw detection in metals are well known. One type of prior art probe includes a single port, i.e., one set of terminals where both the excitation is applied and an impedance change or a resonant frequency change produced by the presence of a flaw is measured. Single port probes are shown, for example, in U.S. Pat. No. 4,286,216, issued Aug. 25, 1981, Auld et al., Great Britain Pat. No. 1,272,409, published Apr. 26, 1972, Shaternikov et el., and in articles by J. P. Watjen and A. J. Bahr, Evaluation of a Novel Eddy-Current Probe For Detecting Cracks Inside and at the Edges of Holes, "Review of Progress in Quantitative Nondestructive Evaluation, Vol. 2B," D. O. Thompson and D. E. Chimenti, eds., Plenum Press, New York (1983), pp. 1187–1202 and Evaluation of an Eddy-Current Tape-Head Probe, "Review of Progress in Quantitative Nondestructive Evaluation, Vol. 3A", D. O. Thompson and D. E. Chimenti, eds., Plenum Press, New York (1984), pp. 663–674.

Another type of probe, identified as a reflection probe, includes two sets of ports, one for excitation and one for detection. A prior art reflection type probe is illustrated in FIG. 1 of the drawings. Prior art reflection probes include differentially wound detection coils such that in the absence of a flaw, equal voltages of opposite phase are induced therein. The presence of a flaw perturbs the voltage in one pickup, or detection, coil to a greater extent than the voltage change in the other detection coil for a change in the output from the detection port.

OBJECTS AND SUMMARY OF THE INVENTION

An object of this invention is the provision of an eddy current probe and method having high spatial resolution, high sensitivity, and good lift-off discrimination.

Another object of this invention is the provision of a reflection-type eddy current probe which is completely compatible with conventional eddy-current instruments.

Another object of this invention is the provision of a reflection-type eddy current probe in which edge effects are minimized whereby small flaws on surfaces and close to edges and corners are readily discernible.

Another object of this invention is the provision of an eddy current probe which is readily adapted to be formed in a wide variety of configurations using established fabrication technology.

Another object of this invention is the provision of an eddy-current probe which includes an integral holder to facilitate engagement of the probe with the edge of an object under test and to facilitate movement of the probe along said edge.

The above and other objects and advantages of this invention are achieved by use of a probe which includes a pair of ferrite cores having in-line gaps in close proximity to each other. A non-magnetic holder supports the cores in a fixed relative position, and closes the core gaps. Each ferrite core is provided with separate excitation and detection windings. The excitation windings are connected in parallel or in series to an rf voltage or current source for energizing the same. The detection windings, which are differentially wound on the ferrite cores, are connected to a voltage detecting instrument. The ferrite cores at the in-line gaps are directly engageable with the metal test object, and as the probe is scanned over a flaw in the object, the detection winding voltages are unbalanced, which unbalance is sensed by the associated voltage measuring instrument. The insulating holder is provided with a profile which conforms to that of an edge portion of the object to be examined to facilitate movement of the probe along said edge.

BRIEF DESCRIPTION OF THE DRAWINGS

The invention, together with objects and advantages thereof, will be better understood from the description when considered in conjunction with the drawings. In the drawings, wherein like reference characters refer to the same parts in the several views:

Reference first is made to FIG. 1 wherein a prior art reflection probe is shown comprising an energizing winding 10 which is adapted for connection to an rf source, not shown, together with a separate sensing, or pick-up winding 12 which is adapted for connection to voltage detecting means, not shown. A metallic test piece 14 is scanned by the probe for the production of eddy currents. The detector winding 12 is differentially wound such that equal, opposite polarity, voltages are induced therein when the probe is located adjacent an unflawed surface area of the test piece. The source winding 10 and detector winding 12 function as transformer primary and secondary windings, respectively, and FIG. 1A shows an approximate equivalent circuit for the probe. This circuit is termed a transformer hybrid; because its secondary is differentially wound, the circuit has the property that application of a voltage across the primary ideally produces zero voltage across the secondary. The differential construction of the secondary minimizes the effect of symmetric changes in the probe environment, such as vertical lift-off; whereas asymmetric disturbance, such as produced by a surface flaw, upsets the differential balance and produces a large output.

Figure 2:
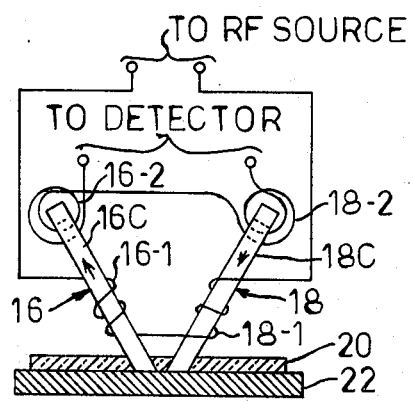
FIG. 2 is a diagrammatic front view of a reflection probe which embodies the present invention, with part of the supporting structure shown broken away for clarity.
Figure 4:
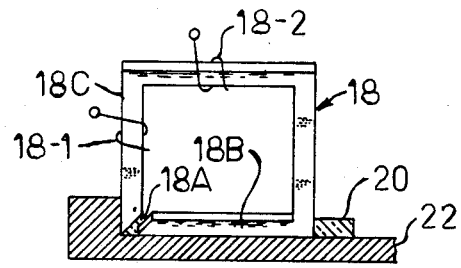
FIG. 4 is a side view of the probe shown in FIG. 2, with part of the supporting structure shown broken away for clarity.
Figure 3:
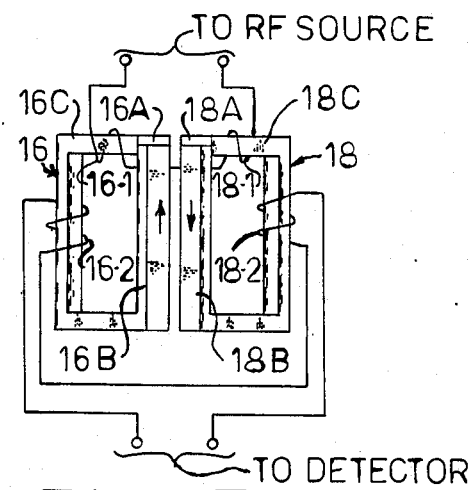
FIG. 3 is a bottom view of the probe shown in FIG. 2, but without the supporting structure.

Reference now is made to FIGS. 2–4 of the drawings wherein the novel probe of this invention is shown comprising first and second ferrite cores 16 and 18 formed with in-line gaps 16A and 18A, respectively. Together, the ferrite cores form a generally V-shape, as seen in FIG. 2, and are held in the V-shape configuration by means of a non-magnetic, nonconducting, holder 20 formed of glass, plastic, ceramic, or like material. The in-line gaps 16A and 18A are filled with the holder material. Base legs 16B and 18B of the ferrite cores are closely spaced, and the bottom edges of these legs are flush with the bottom face of the holder 20.

In the probe of FIGS. 2–4, the in-line gaps 16A and 18A are located at one end of the base legs 16B and 18B, between the base legs and associated upwardly extending legs 16C and 18C, respectively. The free ends of upwardly extending legs 16C and 18C and base legs 16B and 18B are chamfered to provide for upwardly inclined magnetic flux gaps which extend to the outer free edges of legs 16C and 18C. This arrangement is well adapted for surface flaw detection adjacent inside corners of pieces under test, such as test piece 22.

Figure 5:
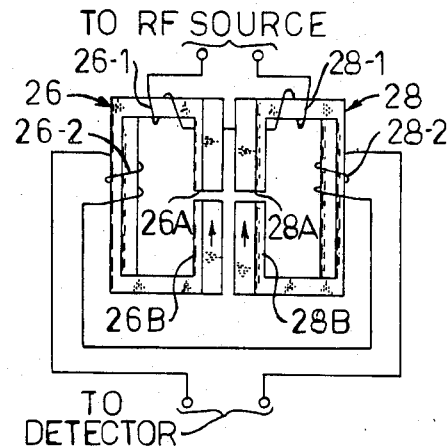
FIG. 5 is a bottom view similar to FIG. 3 but showing a modified form of probe in which magnetic fields are generated in opposite directions.

Each ferrite core 16 and 18 carries a pair of windings 16-1 and 16-2, and 18-1 and 18-2, respectively. Windings 16-1 and 18-1 are connected in series to an rf source, not shown. Together, windings 16-1 and 18-1 comprise the probe excitation winding for generation of high frequency magnetic flux fields within the ferrite cores 16 and 18 and across the associated gaps 16A and 18A. The ferrite cores, which are of relatively high resistance, low reluctance material, directly engage the test piece 22 at the in-line gaps 16A and 18A, whereby strong magnetic fields are set up on the test piece 22. In the arrangement illustrated in FIGS. 2–4, the excitation windings 16-1 and 18-1 are wound such that the magnetic fields are generated in opposite directions at the gaps to provide for an antisymmetric-field probe. A symmetric-field probe is shown in FIG. 5 and described herein below. Arrows on the cores indicate instantaneous magnetic field directions in the ferrite cores 16 and 18 produced by the excitation windings 16-1 and 18-1, respectively. The permeability of the ferrite cores is sufficiently large to insure that the reluctance of the gaps 16A and 18A is much larger than the reluctance of the remainder of the magnetic circuits. The probe is of the non-resonant type, whereby a wide range of rf frequencies may be employed from, say, 200 to 5,000 KHz, for exciting the same. It here will be noted that although series connected excitation winds 16-1 and 18-1 are shown, parallel connection thereof may be employed. Also, either an rf current or voltage source may be used for energization of the windings 16-1 and 18-1. Although a current source may be preferred, a broadband current source may not be as readily available as a broadband voltage source.

The detection windings 16-2 and 18-2 are connected in series to a detector, not shown. Flaw detector instruments for use with prior art reflection probes may be used in the operation of the novel probes of this invention. One such suitable instrument is the NDT-18 eddyscope by Nortec Corporation, Kennewick, Wash.

Figure 1:
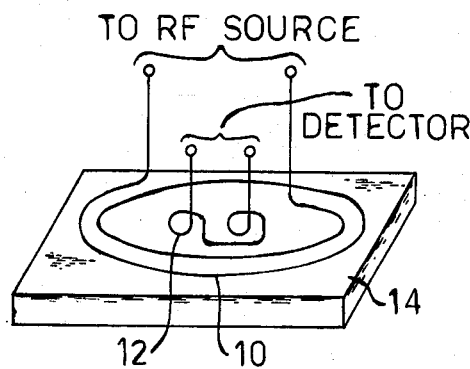
FIG. 1 diagrammatically illustrates a prior art reflection probe for flaw detection.
Figure 1A:
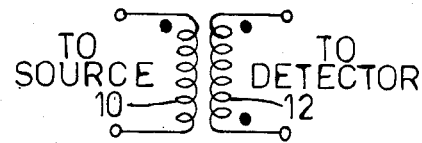
FIG. 1A shows an approximate equivalent circuit for the reflection probe of FIG. 1.

The series-connected detection windings 16-2 and 18-2 are differentially wound such that, ideally, zero voltage is produced at the input to the detector in the absence of an asymmetric disturbance adjacent the core gaps. The number of turns employed on the excitation and detector windings is selected for optimum matching with the rf source and detector. An advantage of the present reflection probe is that its ferrite core construction permits a wider choice for the number of excitation and detection winding turns than do prior art coil-type design such as illustrated in FIG. 1.

In operation, the probe is placed directly in contact with the test piece 22 and mechanically scanned along the surface thereof. As noted above, the conductivity of the ferrite core material is much less than the conductivity of the material being tested which allows for such direct contact. With the in-line gaps 16A and 18A at one corner of the ferrite cores, testing at sharp internal corners, such as seen in FIG. 3, is possible. The presence of a flaw in the material at one of the magnetic fields results in an unbalance in the voltages produced in the detector windings 16-1 and 18-2 for production of an output at the detector port which is sensed by the detector instrument connected thereto.

Reference now is made to FIG. 5 of the drawings wherein a modified form of this invention is shown comprising a pair of ferrite cores 26 and 28 formed with in-line magnetic gaps 26A and 28A in the base legs 26B and 28B, respectively, adjacent the center of the legs; the invention not being limited to use of ferrite cores with magnetic gaps at the core corners. Excitation windings 26-1 and 28-1 on the cores 26 and 28 are connected together and to an rf source. In this embodiment, the windings 26-1 and 28-1 are wound so as to produce magnetic fields in the same direction in the gaps 26A and 28A, which results in a symmetric field probe. Arrows on the cores indicate instantaneous magnetic field directions in the ferrite cores 26 and 28 produced by the excitation windings 26-1 and 28-1, respectively. A nonconducting holder, not shown, such as holder 20 shown in FIGS. 2 and 4, supports the ferrite cores in the illustrated V-shape arrangement, and fills the gaps 26A and 28A.

Series connected detection windings 26-2 and 28-2 on the cores 26 and 28 are differentially wound such that substantially zero voltage is produced at the detector port in the absence of an asymmetric disturbance adjacent the core gaps. In operation, the excitation and detector ports are connected to a suitable rf frequency source and voltage measuring instrument, respectively, and the probe is scanned along the surface of a metallic test piece. Again, a flaw in the surface of the test piece results in an unbalance in voltages produced in the detector windings 26-2 and 28-2, which unbalance is sensed by the measuring instrument connected to the detector port.

Figure 6:
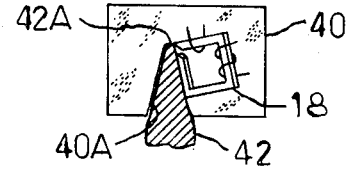
FIG. 6 diagrammatically illustrates the probe shown in FIGS. 2–4 together with a holder which adapts the probe for examination of a knife edge geometry.
Figure 7:
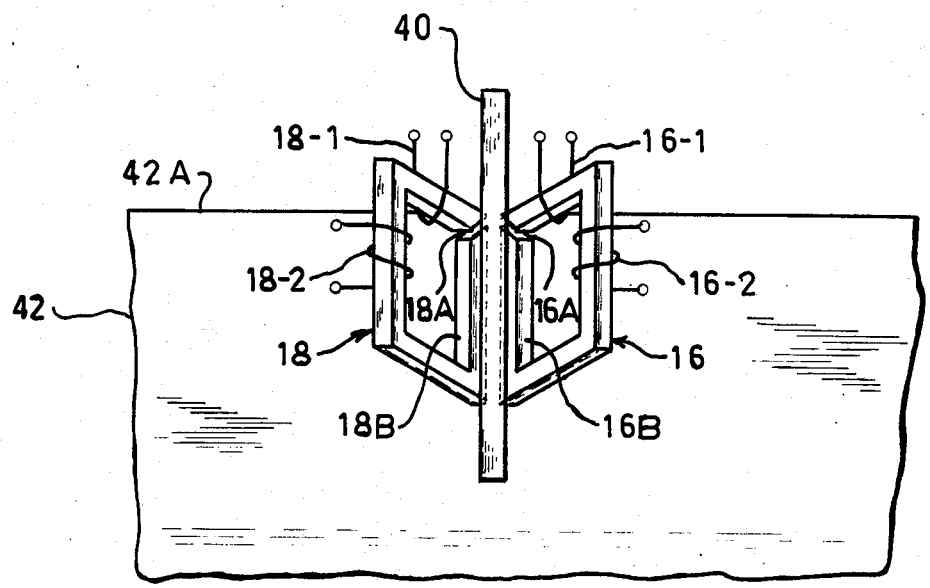
FIG. 7 is a side elevational view of the probe shown in FIG. 6 taken from the right side thereof.
Figure 8:
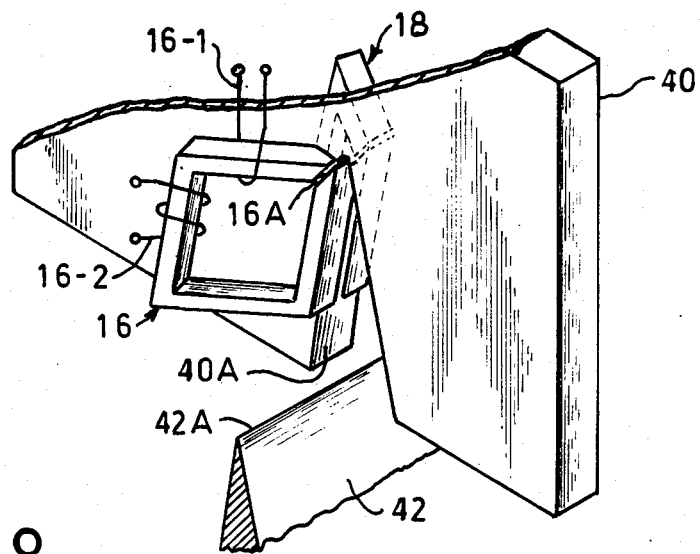
FIG. 8 is a perspective view of the probe shown in FIG. 6 but showing the test piece removed from the holder.

The novel probes of this invention are not limited to the use of holder 20 for support of the ferrite cores. In a modified form of this invention shown in FIGS. 6, 7 and 8, a probe is shown which includes a holder 40 that extends along a plane which bisects the V-shaped core configuration. Again, the holder, or fixture, 40 is formed of a suitable non-conducting, non-magnetic material. Ferrite cores, such as cores 16 and 18, are affixed to the holder and extend outwardly from opposite faces thereof. In FIG. 6, only core 18 is viewable.

A metallic test piece 42 is shown which includes a prominent feature, e.g. knife edge 42A, adapted for inspection by the probe. A cut-out, or opening, 40A is formed in the holder 40 having a profile which conforms to a section of the test piece adjacent the knife edge portion thereof. The probe gaps terminate at the cut-out 40A whereby the ferrite cores, at cut-out 40A, are directly engageable with the testpiece 42 adjacent the knife edge 42A. Guided by the holder 40, the probe is readily moved along the test piece for flaw testing at the knife edge.

The invention having been described in detail in accordance with requirements of the Patent Statutes, other changes and modifications will suggest themselves to those skilled in this art. For example, the ferrite cores included in the probes are not limited to the generally rectangular-shaped cores shown in the drawings. Ferrite is relatively easily machined whereby cores having a wide variety of shapes may be employed, dependent upon the particular flaw testing application. It is intended that the above and other such changes and modifications shall fall within the spirit and scope of the invention as defined in the appended claims.

I claim:

1. A probe for scanning a metal surface of a test piece to test for flaws in the metal surface comprising, first and second ferrite cores each having a narrow gap therein, non-magnetic, non-conducting holder means supporting the cores, the first and second cores together forming a generally V-shape with the core gaps being in-line and adjacent each other, first and second windings on each core, means for connecting said first windings to an rf source for energizing the probe and generating magnetic fields across the core gaps, means for connecting said second windings in series circuit and to voltage detecting means, said second windings being differentially wound on said first and second cores whereby substantially zero voltage is developed at the output from the series connected second windings in the absence of an asymmetric disturbance adjacent the core gaps, said holder means filling said gaps and extending substantially along a plane which bisects the V-shape angle formed by the cores, and means forming a cut-out in said holder means with which said gaps communicate, at least a portion of said cutout conforming to a portion of the surface of the test piece to facilitate scanning the probe along the test piece.

2. A probe as defined in claim 1 including an rf source connected to said first windings for production of simultaneous magnetic fields in the same direction in the core gaps with energization of the first windings by said rf source.

3. A probe as defined in claim 1 including an rf source connected to said first windings for production of simultaneous opposite direction magnetic fields in the core gaps with energization of the first windings by said rf source.

4. A probe as defined in claim 1 wherein said ferrite cores include generally right angle leg portions the ends of which leg portions are chamfered, between which chamfered ends said gaps are formed.

* * * * *